United States Patent
Monden et al.

(10) Patent No.: US 11,220,652 B2
(45) Date of Patent: Jan. 11, 2022

(54) METHOD FOR INSPECTING LUBRICATING OIL COMPOSITION AND METHOD FOR PRODUCING LUBRICATING OIL COMPOSITION

(71) Applicant: SHOWA DENKO K.K., Tokyo (JP)

(72) Inventors: Ryuji Monden, Tokyo (JP); Yu Gao, Tokyo (JP); Masumi Kuritani, Tokyo (JP); Kunio Kondo, Tokyo (JP)

(73) Assignee: SHOWA DENKO K.K., Tokyo (JP)

( * ) Notice: Subject to any disclaimer, the term of this patent is extended or adjusted under 35 U.S.C. 154(b) by 0 days.

(21) Appl. No.: 16/769,085

(22) PCT Filed: Dec. 4, 2018

(86) PCT No.: PCT/JP2018/044552
§ 371 (c)(1),
(2) Date: Jun. 2, 2020

(87) PCT Pub. No.: WO2019/111889
PCT Pub. Date: Jun. 13, 2019

(65) Prior Publication Data
US 2021/0222083 A1    Jul. 22, 2021

(30) Foreign Application Priority Data
Dec. 6, 2017  (JP) ............... JP2017-234587

(51) Int. Cl.
*C10M 177/00* (2006.01)
*C10M 113/02* (2006.01)
(Continued)

(52) U.S. Cl.
CPC ........ *C10M 177/00* (2013.01); *C10M 113/02* (2013.01); *C10M 169/02* (2013.01);
(Continued)

(58) Field of Classification Search
CPC ..... G01N 33/30; G01N 15/02; C10M 113/02; C10M 177/00; C10N 2030/06; C10N 2040/25; C10N 2060/10; C10N 2060/12
See application file for complete search history.

(56) References Cited

U.S. PATENT DOCUMENTS

| 6,432,887 B1 * | 8/2002 | Yamamoto ........... C10M 107/38 508/138 |
| 2011/0034357 A1 | 2/2011 | Kawata et al. |
| 2019/0032971 A1 | 1/2019 | Ishida et al. |

FOREIGN PATENT DOCUMENTS

| CN | 104692463 A | 6/2015 |
| JP | 07-225229 A | 8/1995 |

(Continued)

OTHER PUBLICATIONS

Handbook of lubricant brand name 2012, Lubrication Technology Inc., pp. 341-352.
(Continued)

*Primary Examiner* — Vishal V Vasisth
(74) *Attorney, Agent, or Firm* — Sughrue Mion, PLLC

(57) ABSTRACT

A method for inspecting a lubricant oil composition containing a base oil and a fullerene, the method including: measuring at least one of a lamellar length of the lubricating oil composition and a most abundant diameter in a particle size distribution obtained by a dynamic light scattering method, and selecting the lubricating oil composition whose measured value is within a set range.

8 Claims, 2 Drawing Sheets

(51) Int. Cl.
  *C10M 169/02* (2006.01)
  *G01N 15/02* (2006.01)
  *G01N 33/28* (2006.01)
  *C10N 70/00* (2006.01)

(52) U.S. Cl.
  CPC ......... *G01N 15/02* (2013.01); *G01N 33/2888* (2013.01); *C10M 2201/0416* (2013.01); *C10M 2203/003* (2013.01); *C10N 2070/00* (2013.01)

(56) References Cited

FOREIGN PATENT DOCUMENTS

| | | |
|---|---|---|
| JP | 10-170505 A | 6/1998 |
| JP | 2008-266501 A | 11/2008 |
| JP | 2016-180465 A | 10/2016 |
| WO | 2016/159079 A1 | 10/2016 |
| WO | 2017/141825 A1 | 8/2017 |
| WO | 2018/150806 A1 | 8/2018 |

OTHER PUBLICATIONS

International Search Report for PCT/JP2018/044552 dated Mar. 12, 2019.
Extended European Search Report dated Aug. 13, 2021 in European Application No. 18885007.7.

\* cited by examiner

METHOD FOR INSPECTING LUBRICATING OIL COMPOSITION AND METHOD FOR PRODUCING LUBRICATING OIL COMPOSITION

CROSS-REFERENCE TO RELATED APPLICATIONS

This application is a National Stage of International Application No. PCT/JP2018/044552 filed on Dec. 4, 2018, which claims priority under U.S.C. § 119(a) to Japanese Patent Application No. 2017-234587 filed on Dec. 6, 2017, the disclosure of which is incorporated herein in its entirety by reference.

TECHNICAL FIELD

The present invention relates to a method for inspecting a lubricating oil composition and a method for producing a lubricating oil composition.

Priority is claimed on Japanese Patent Application No. 2017-234587, filed Dec. 6, 2017, the content of which is incorporated herein by reference.

BACKGROUND ART

In recent years, with the increase in speed, efficiency, and energy saving, there is a strong demand for improved performance of lubricating oils used in automobiles, home appliances, industrial machines, and the like. Various additives such as antioxidants, extreme pressure additives, rust inhibitors, corrosion inhibitors and the like are blended in lubricating oil compositions in order to improve the characteristics so as to be suitable for their applications.

In order to meet these demands, an additive composition for engine lubricating oil has been known, in which nanocarbon particles (fullerenes), organic solvents, viscosity index improvers, friction modifiers, and detergent dispersants are added to a lubricating base oil such as mineral oil or ester oil in order to simultaneously improve multiple performances such as low friction, increased torque, and fuel saving (for example, see Patent Document 1).

Furthermore, fullerenes may be added to lubricating oil compositions used in refrigerant compressors (for example, see Patent Document 2).

In general, the friction coefficient and so on are important characteristics of lubricating oil compositions, but their measurement is time consuming. For this reason, in the production process of lubricating oil compositions, the characteristics of the lubricating oil compositions are identified by using indicators such as density, kinematic viscosity, viscosity index, pour point, and total oxidation, which are easy to measure (for example, see Non-Patent Document 1).

CITATION LIST

Patent Document

[Patent Document 1] Japanese Unexamined Patent Application, First Publication No. 2008-266501
[Patent Document 2] PCT International Patent Publication No. 2017/141825

Non-Patent Document

[Non-Patent Document 1] Handbook of lubricant brand name 2012, Lubrication Technology Inc., pp. 341-352

SUMMARY OF INVENTION

Problem to be Solved by the Invention

However, in the case of the lubricating oil composition containing a fullerene described in Non-patent Document 1 and the like, even if product management was performed using the above indicators, a product stably reproducing lubricating characteristics such as a friction coefficient could not be obtained. That is, even if the characteristics of the product were quantified by the above indicators and the product falling within a certain range was accepted, the lubricating characteristics varied beyond an allowable range in some cases.

In addition, by measuring the lubricating characteristics of the products of the lubricating oil composition, it is possible to select the products whose lubricating characteristics are within the allowable range. However, in order to measure the lubricating characteristics of the lubricating oil composition, it is necessary to perform a friction test such as a ball-on-disk test for each product lot. In this case, it takes more labor and time, and the cost of a test board or the like increases. For this reason, the friction test is not suitable to be performed for each production lot.

The present invention has been made in view of the above circumstances, with an object of providing a method for inspecting a lubricating oil composition and a method for producing a lubricating oil composition that can stably reproduce the frictional characteristics by using a method that is relatively easy to measure, even if the lubricating oil composition contains a fullerene.

Means for Solving the Problem

[1] A method for inspecting a lubricating oil composition containing a base oil and a fullerene, the method including:
measuring at least one of a lamellar length of the aforementioned lubricating oil composition and a most abundant diameter in a particle size distribution obtained by a dynamic light scattering method; and
selecting the aforementioned lubricating oil composition whose measured value is within a set range.

[2] The method for inspecting a lubricating oil composition according to [1],
wherein the aforementioned lamellar length and the aforementioned most abundant diameter are measured, and
the aforementioned lubricating oil composition having both measured values within set ranges is selected.

[3] A method for producing a lubricating oil composition including a step of selecting a lubricating oil composition obtained by mixing a base oil and a fullerene by the method for inspecting a lubricating oil composition according to [1] or [2].

Effects of the Invention

According to the present invention, it is possible to provide a method for inspecting a lubricating oil composition and a method for producing a lubricating oil composition that can stably reproduce the frictional characteristics using a method that is relatively easy to measure, even if it is a lubricating oil composition containing a fullerene.

DESCRIPTION OF EMBODIMENTS

Figure 1:
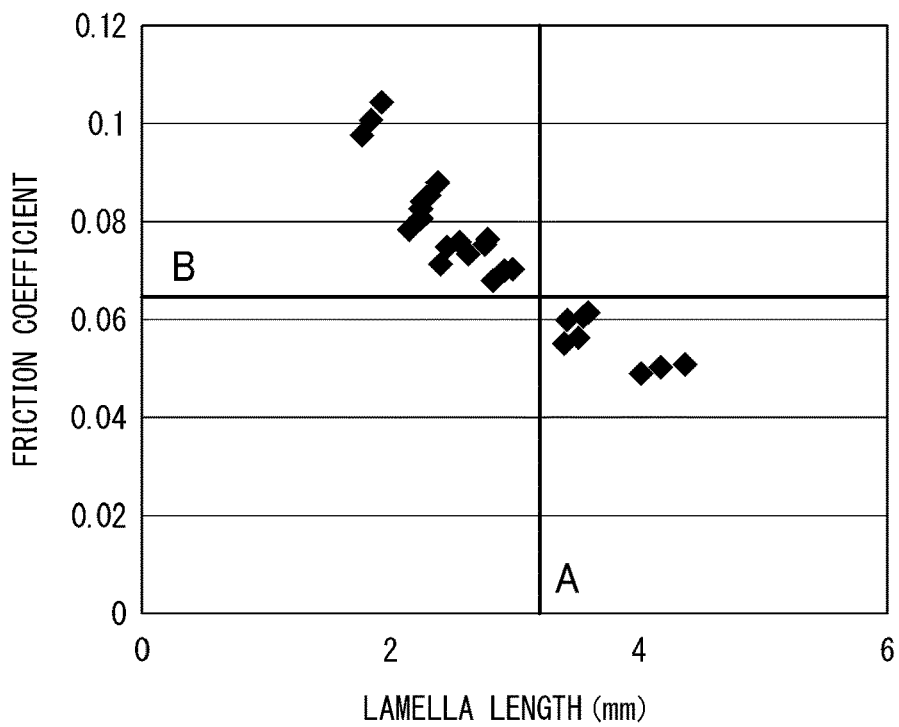
FIG. 1 is a view showing a relationship between a lamellar length of a lubricating oil composition and a friction coefficient in Example 1.

Embodiments of the method for inspecting a lubricating oil composition and the method for producing a lubricating oil composition according to the present invention will be described.

It should be noted that the present embodiment is specifically described for better understanding of the spirit and scope of the invention. The present embodiment does not limit the present invention unless otherwise specified.

[Method for Inspecting Lubricating Oil Composition]

The method for inspecting a lubricating oil composition of the present embodiment is a method for inspecting a lubricating oil composition containing a base oil and a fullerene. The method for inspecting a lubricating oil composition of the present embodiment is a method for measuring at least one of the lamellar length of the lubricating oil composition and the most abundant diameter in the particle size distribution obtained by the dynamic light scattering method, and selecting the lubricating oil composition whose measured value is within a set range.

(Lubricating Oil Composition)

The lubricating oil composition inspected by the method for inspecting a lubricating oil composition of the present embodiment contains a base oil and a fullerene.

(Base Oil)

The base oil contained in the lubricating oil composition of the present embodiment is not particularly limited, and mineral oils and synthetic oils, which are generally widely used as base oils for lubricating oils, are suitably used.

Mineral oil used as a lubricating oil is generally converted to saturated hydrocarbons by saturating the carbon-carbon double bonds contained therein by hydrogenation. Examples of such mineral oils include paraffinic base oils and naphthenic base oils.

Examples of synthetic oils include synthetic hydrocarbon oils, ethereal oils and ester oils. More specifically, poly-α-olefins, diesters, polyalkylene glycols, polyalphaolefins, polyalkyl vinyl ethers, polybutenes, isoparaffins, olefin copolymers, alkylbenzenes, alkylnaphthalenes, diisodecyl adipate, monoesters, dibasic acid esters, tribasic acid esters, polyol esters (trimethylolpropane caprylate, trimethylolpropane pelargonate, pentaerythritol 2-ethylhexanoate, pentaerythritol pelargonate, and the like), dialkyl diphenyl ethers, alkyl diphenyl sulfides, polyphenyl ethers, silicone lubricating oil (dimethyl silicone, and the like), perfluoropolyethers, and the like are suitably used.

Among these synthetic oils, poly-α-olefins, diesters, polyol esters, polyalkylene glycols, and polyalkyl vinyl ethers are more preferably used.

One of these mineral oils and synthetic oils may be used alone, or two or more types of oils selected from them may be used by mixing at an arbitrary ratio.

(Fullerene)

The structure and production method of the fullerene contained in the lubricating oil composition in the present embodiment are not particularly limited, and various types of fullerenes can be used. Examples of the fullerene include $C_{60}$ and $C_{70}$ which are relatively easily available, higher fullerenes, and a mixture thereof. Among fullerenes, $C_{60}$ and $C_{70}$ are preferable from the viewpoint of high solubility in lubricating oil, and $C_{60}$ is more preferable from the viewpoint of less coloration to lubricating oil. When a mixture of two or more types of fullerenes is used as the fullerene, $C_{60}$ is preferably contained in an amount of 50% by mass or more.

Further, the fullerene may be chemically modified for the purpose of further increasing the solubility in the base oil, and the like. Examples of the chemically modified fullerene include methanofullerenes (phenyl $C_{61}$ butyric acid methyl ester ([60] PCBM), diphenyl $C_{62}$ dibutyric acid methyl ester (=Bis [60] PCBM), phenyl C butyric acid methyl ester ([70] PCBM), phenyl $C_{85}$ butyric acid methyl ester ([85] PCBM), phenyl $C_{61}$ butyric acid butyl ester ([60] PCBB), phenyl C butyric acid octyl ester ([60] PCBO)), indene adducts of fullerenes, fullerene hydroxides, and pyrrolidine derivatives of fullerenes.

(Additive)

The lubricating oil composition of the present embodiment may contain an additive other than the base oil and the fullerene as long as the effects of the present embodiment are not impaired.

The additive to be added to the lubricating oil composition in the present embodiment is not particularly limited. Examples of the additive include commercially available antioxidants, viscosity index improvers, extreme pressure additives, detergent dispersants, pour point depressants, corrosion inhibitors, solid lubricants, oiliness improvers, rust inhibitors, demulsifiers, defoamers, and hydrolysis inhibitors. One of these additives may be used alone, or two or more types thereof may be used in combination.

As the additive, a compound having an aromatic ring is preferable because the fullerene is easily dissolved.

Examples of the antioxidant having an aromatic ring include dibutylhydroxytoluene (BHT), butylhydroxyanisole (BHA), 2,6-di-tert-butyl-p-cresol (DBPC), 3-arylbenzofuran-2-one (intramolecular cyclic ester of hydroxycarboxylic acid), phenyl-α-naphthylamine, dialkyldiphenylamine, and benzotriazole.

Examples of the viscosity index improver having an aromatic ring include polyalkylstyrenes and hydride additives of styrene-diene copolymers.

Examples of the extreme pressure additive having an aromatic ring include dibenzyl disulfide, allyl phosphate, allyl phosphite, amine salts of allyl phosphate, allyl thiophosphate, amine salts of allyl thiophosphate, and naphthenic acid.

Examples of the detergent dispersant having an aromatic ring include benzylamine succinic acid derivatives and alkylphenolamines.

Examples of the pour point depressant having an aromatic ring include chlorinated paraffin-naphthalene condensates, chlorinated paraffin-phenol condensates, and polyalkylstyrenes.

Examples of the demulsifier having an aromatic ring include alkylbenzene sulfonates and the like.

Examples of the corrosion inhibitor having an aromatic ring include dialkyl naphthalene sulfonates and the like.

The lubricating oil composition in the present embodiment can be used for various applications such as industrial gear oil; hydraulic oil; compressor oil; refrigerating machine oil; cutting oil; plastic working lubricant including rolling oil, press oil, forging oil, deep drawing oil, drawing oil, and punching oil; metalworking fluids such as heat treating oil and electrical discharge machining oil; sliding guide surface oil; bearing oil; rust preventive oil; and heating medium oil.

(Inspection Method)

In the method for inspecting a lubricating oil composition of the present embodiment, at least one of the lamellar length of the lubricating oil composition and the most abundant diameter in the particle size distribution obtained by the dynamic light scattering method is measured. It should be noted that in the measurement of the particle size distribution, the particle size distribution of the fullerene dissolved or dispersed in the base oil and the aggregated particles thereof is measured.

(Lamellar Length Measurement)

The lamellar length of the lubricating oil composition is measured by a known method called a ring method. In other words, it is measured by a method in accordance with the surface tension test method specified in the Japanese Industrial Standard JIS K2241: 2000 7.3.

More specifically, a ring lifted parallel to the liquid to be measured (lubricating oil composition) is submerged once in the liquid, and then the ring is gradually pulled apart in the vertical direction. At this time, a liquid film formed between the ring and the liquid surface exerts a force to lower the ring. This force, after showing the maximum value (that is, surface tension), gradually decreases with an increase in the pulling amount, and finally becomes zero at the point where the liquid film breaks. Here, the movement distance of the ring from the point where the force for lowering the ring shows the maximum value to the point where the liquid film breaks is defined as the lamellar length. It should be noted that these expressions "lifting" and "lowering" of the ring represent relative movements with respect to the liquid to be measured. For example, a stage on which the liquid to be measured is placed (hereinafter, may be simply referred to as "stage") may be moved while fixing the ring.

In order to stably measure the lamellar length, the moving speed of the ring is set within a certain range. If the moving speed of the ring is too fast, the liquid film breaks before it is fully extended. On the other hand, if the moving speed of the ring is too slow, the components of the liquid film evaporate, and the liquid film breaks before it is fully extended. In both cases, the lamellar length is measured to be short, because the liquid film breaks before it is fully extended, and the liquid film is destroyed.

Although the optimum conditions for the moving speed of the ring differ depending on the characteristics of the liquid to be measured, a representative sample is selected from among the samples to be measured, a preliminary experiment using the following range as a guide is performed, and the conditions such as the moving speed of the ring at which the maximum lamellar length value is obtained are employed.

The ring lifting speed (stage lowering speed) serving as a reference is preferably from 0.01 mm/sec to 5.0 mm/sec, and more preferably from 0.1 mm/sec to 1.0 mm/sec. The immersion distance of the ring into the liquid is preferably from 0.1 mm to 50 mm, and more preferably from 1 mm to 10 mm.

(Particle Size Distribution Measurement)

The dynamic light scattering method is used for measuring the particle size distribution of the lubricating oil composition because it is suitable for the purpose of measuring the particle size distribution in the nanometer range. More specifically, the method of Examples described later is used.

From the obtained volume-based particle size distribution (also referred to as volume distribution), a particle diameter (referred to as "most abundant diameter") showing the maximum value (highest abundance/frequency) is obtained.

In the method for inspecting a lubricating oil composition of the present embodiment, at least one of the lamellar length of the lubricating oil composition and the most abundant diameter in the particle size distribution obtained by the dynamic light scattering method is measured, and the lubricating oil composition whose measured value is within a set range (a certain range) is accepted, and the lubricating oil composition whose measured value is outside the set range is rejected. As a result, the lubricating oil compositions are sorted.

It should be noted that the certain range of the measured value is set to be a desired range of the friction coefficient from the relationship between the friction coefficient and the lamellar length or the most abundant diameter as shown in Examples described later.

Further, in the method for inspecting a lubricating oil composition of the present embodiment, it is preferable to measure the lamellar length of the lubricating oil composition and the most abundant diameter in the particle size distribution obtained by the dynamic light scattering method, and to select the lubricating oil composition in which both of these measured values are within the set ranges. As described above, by measuring the lamellar length and the most abundant diameter and selecting the lubricating oil composition in which the two measured values are within the set ranges, the accuracy of the selection can be further improved. As a result, the frictional characteristics of the lubricating oil composition can be reproduced more stably.

Further, in the method for inspecting a lubricating oil composition of the present embodiment, as described in Non-Patent Document 1, the density, dynamic viscosity, viscosity index, pour point, total oxidation, and the like of the lubricating oil composition can also be measured.

According to the method for inspecting a lubricating oil composition of the present embodiment, even if the lubricating oil composition contains a fullerene, the frictional characteristics can be stably reproduced by using a relatively easy method of measuring at least one of the lamellar length of the lubricating oil composition and the most abundant diameter in the particle size distribution obtained by the dynamic light scattering method.

[Method for Producing Lubricating Oil Composition]

The method for producing a lubricating oil composition of the present embodiment comprises a step of selecting a lubricating oil composition obtained by mixing a base oil and a fullerene by the method for inspecting a lubricating oil composition of the present embodiment.

In detail, the method for producing a lubricating oil composition of the present embodiment comprises, (1) a step of obtaining a lubricating oil composition which is a mixture of the base oil and the fullerene by mixing the base oil and the fullerene, dissolving a soluble component of the fullerene in the base oil, and undergoing filtration, heat treatment, and the like, as necessary (hereinafter, referred to as "pretreatment step"); and (2) a step of selecting the lubricating oil composition by measuring and quantifying the physical characteristics (lamellar length and/or most abundant diameter) of the lubricating oil composition, accepting the lubricating oil composition having each measured value within the set range, and rejecting the lubricating oil composition having each measured value outside the set range (hereinafter referred to as "inspection step").

The method for producing a lubricating oil composition of the present embodiment may further comprises, if necessary, (3) a step of obtaining a new lubricating oil composition by mixing lubricating oil compositions produced in a plurality of different production batches so as to be selected as acceptable in the "inspection step" (hereinafter referred to as the "post-treatment step").

Hereinafter, the method for producing a lubricating oil composition of the present embodiment will be described in detail.

(Pretreatment Step)

The raw material fullerene is added to the base oil and subjected to a dispersion treatment for 1 hour to 48 hours using a dispersion means such as a stirrer at near room temperature or with heating as necessary.

Examples of the dispersion means for dispersing the fullerene in the base oil include a stirrer, an ultrasonic dispersing device, a homogenizer, a ball mill and a bead mill.

In this manner, a liquid in which the fullerene is dissolved or dispersed in the base oil (sometimes referred to as "fullerene solution") is obtained.

It should be noted that the amount of the fullerene to be added may be an amount at which the concentration of the fullerene in the fullerene solution becomes a desired concentration. Further, in the case where a step of removing an insoluble component described later is provided in the pretreatment step, the amount of fullerene removed by this step is also taken into account, and a larger amount of fullerene is added. In general, the fullerene concentration in the fullerene solution ranges from 1 ppm by mass to 1% by mass.

Alternatively, a fullerene solution having a higher concentration than a desired concentration may be obtained and diluted with a base oil to obtain a fullerene solution having the desired concentration.

The fullerene solution obtained as described above may be used as it is as a lubricating oil composition.

Furthermore, it is preferable that a step of removing an insoluble component is provided in the pretreatment step, and the fullerene solution from which the insoluble component has been removed is used as the lubricating oil composition. It is preferable that the step of removing an insoluble component is preferably provided after the dispersion treatment for dispersing the fullerene in the base oil in the pretreatment step.

Examples of the step of removing an insoluble component include: (1) a removing step using a membrane filter; (2) a removing step using a centrifugal separator; and (3) a removing step using a combination of a membrane filter and a centrifugal separator. Among these removing steps, from the viewpoint of filtration time, the removing step (1) using a membrane filter is preferable when a small amount of lubricating oil composition is obtained, and the removing step (2) using a centrifugal separator is preferable when a large amount of lubricating oil composition is obtained.

It should be noted that in the pretreatment step, especially when heating the fullerene solution, it is preferable to perform the heating operation in a non-oxidizing atmosphere. For example, by replacing the inside of the container storing the fullerene solution with an inert gas, such as nitrogen gas or argon gas, or by further bubbling the fullerene solution in the container with an inert gas, it is preferable to bring the fullerene solution to an equilibrium state with the inert gas.

(Inspection Step)

In the method for producing a lubricating oil composition of the present embodiment, the inspection step is a step of selecting a lubricating oil composition by the method for inspecting a lubricating oil composition of the present embodiment.

(Post-Treatment Step)

For each lubricating oil composition produced in a plurality of different production batches, at least one of the measurement of the lamellar length and the measurement of the particle size distribution is performed. As a result, at least one of the lamellar length and the most abundant diameter in the particle size distribution with respect to the production batch can be ascertained, and the lubricating oil composition can be classified based on these measured values.

By classifying the lubricating oil composition, the following effects can be obtained.

(1) A lubricating oil composition in which at least one of the lamellar length and the most abundant diameter in the particle size distribution is rejected can be excluded.

(2) A lubricating oil composition which may become newly acceptable can be obtained by mixing a plurality of different lubricating oil compositions in which at least one of the lamellar length and the most abundant diameter in the particle size distribution falls within the rejected range.

(3) A new lubricating oil composition can be obtained by mixing a plurality of different lubricating oil compositions in which at least one of the lamellar length and the most abundant diameter in the particle size distribution falls within the acceptable range.

As described above, according to the method for producing a lubricating oil composition of the present embodiment, even if the lubricating oil composition contains a fullerene, a lubricating oil composition having a small deviation in frictional characteristics between production batches can be obtained by using a relatively easy method of measuring at least one of the lamellar length of the lubricating oil composition and the most abundant diameter in the particle size distribution obtained by the dynamic light scattering method.

The friction coefficient of a lubricating oil composition is an important factor for evaluating the frictional characteristics and lubricating characteristics of the lubricating oil composition. However, the measurement of the friction coefficient is time consuming.

The inventors of the present invention have found that the lamellar length of the lubricating oil composition and the most abundant diameter in the particle size distribution according to the dynamic light scattering method are numerical values having a correlation with the friction coefficient of the lubricating oil composition, and can be used as indicators of the friction coefficient of the lubricating oil composition, as described later. That is, if the numerical value of the lamellar length of the lubricating oil composition and/or the most abundant diameter is within a specific range, it can be said that the friction coefficient of the lubricating oil composition is within a specific range corresponding to the numerical value of the lamellar length and/or the most abundant diameter.

The measurement of the lamellar length of the lubricating oil composition and/or the most abundant diameter is easier than the measurement of the friction coefficient. Therefore, by using the measured value of the lamellar length of the lubricating oil composition and/or the most abundant diameter as an indicator of the friction coefficient, the friction coefficient of the lubricating oil composition can be easily and efficiently evaluated without performing a troublesome measurement of the friction coefficient. Further, an evaluation method for evaluating the friction coefficient of a lubricating oil composition by using the measured value of the lamellar length of the lubricating oil composition and/or the most abundant diameter is useful because it is easy to determine whether or not the lubricating oil composition has an appropriate friction coefficient according to the application or the like without measuring the friction coefficient.

Preferred embodiments of the present invention have been described above in detail. However, the present invention is not limited to these specific embodiments, and various changes and modifications can be made within the scope of the present invention described in the claims.

EXAMPLES

Hereinafter, the present invention will be described more specifically with reference to Examples and Comparative Examples. The present invention is not limited to the following Examples.

(Production of Lubricating Oil Composition)

A base oil was obtained by mixing mineral oil A (product name: Diana Fresia P-22, manufactured by Idemitsu Kosan Co., Ltd.) and mineral oil B (product name: Diana Fresia P-32, manufactured by Idemitsu Kosan Co., Ltd.) at a mass ratio of 1:1.

Next, 50 g of the base oil and 0.003 g (30 mg) of a fullerene raw material (nanom) mix ST manufactured by Frontier Carbon Corporation, a mixture of $C_{60}$: 60% by mass and $C_{70}$: 25% by mass, with the remainder being other higher fullerenes) were mixed and stirred at room temperature using a stirrer for the time shown in Table 1.

After completion of stirring, the resulting mixture was used as it was or filtered by passing it through a membrane filter having a mesh size shown in Table 1 to obtain a fullerene solution.

Next, the obtained fullerene solution was diluted 5-fold with a base oil to obtain a lubricating oil composition.

Nine types of lubricating oil compositions No. 1 to No. 9 obtained in this manner as shown in Table 1 were prepared under the conditions marked with open circles in the table, and three samples were prepared for each type. In other words, a total of 27 samples were prepared.

TABLE 1

| Lubricating oil composition No. | Stirring time [hour] | | | Filtration [mesh µm] | | |
|---|---|---|---|---|---|---|
| | 1 | 5 | 36 | None | 1 | 0.1 |
| 1 | | | o | | | o |
| 2 | | | o | | o | |
| 3 | | | o | o | | |
| 4 | | o | | | | o |
| 5 | | o | | | o | |
| 6 | | o | | o | | |
| 7 | o | | | | | o |
| 8 | o | | | | o | |
| 9 | o | | | o | | |

(Measurement of Kinematic Viscosity)

About 50 mL of the lubricating oil composition was taken out into a glass beaker, and this beaker was immersed in a water bath at 40° C. for 30 minutes.

Next, the kinematic viscosity of the lubricating oil composition was measured by a method conforming to the method for measuring the viscosity of liquids using a capillary viscometer specified in the Japanese Industrial Standard JIS Z8803: 2011.

(Measurement of Lamellar Length)

The lamellar length was measured by a method in accordance with the surface tension test method specified in the Japanese Industrial Standard JIS K2241: 2000 7.3. That is, using a surface tensiometer (model: DY-500, manufactured by Kyowa Interface Science Co., Ltd.), about 20 mL of the lubricating oil composition was taken out into a glass petri dish (depth: 20 mm, inner diameter: 75 mm) and placed on the stage of the surface tensiometer. Using a ring made of platinum and having a diameter of 14.4 mm, the tension applied to the ring was measured by setting the stage lifting speed to 0.7 mm/sec, the stage lowering speed to 0.1 mm/sec, and the immersion distance of the ring into the lubricating oil composition to 2.5 mm. From the graph of the stage position and the tension applied to the ring obtained by the measurement, the movement distance of the stage from the point where the force lowering the ring showed the maximum value to the point where the liquid film broke and the force became zero was calculated as the lamellar length. It should be noted that this measurement was performed in an environment of 25±2° C.

(Measurement of Most Abundant Diameter)

About 20 mL of the lubricating oil composition was taken out into a 1 mm square glass cell, and the particle size distribution by dynamic light scattering was measured using a zeta potential/particle size/molecular weight measurement system (model: ELSZ-2000ZS, manufactured by Otsuka Electronics Co., Ltd.). The particle diameter at which the obtained volume-based particle size distribution had the maximum value was defined as the most abundant diameter.

(Measurement of Friction Coefficient)

The frictional characteristics of the obtained lubricating oil composition were evaluated using a friction and wear tester (product name: ball-on-disk tribometer, manufactured by Anton Paar GmbH).

The material of the substrate and balls constituting the friction and wear tester was a high carbon chromium bearing steel material SUJ2. It should be noted that the ball has a diameter of 6 mm, and a contact surface with the substrate is scraped in advance to form a circular shape having a diameter of 2 mm.

The lubricating oil composition was applied to one main surface of the substrate.

Next, the balls were slid through the lubricating oil composition on one main surface of the substrate so that the balls followed concentric circular orbits. The speed of the ball on one main surface of the substrate was set to 50 cm/sec, and the load applied onto one main surface of the substrate by the ball was set to 10 N. The average value of a torque meter when the integrated sliding distance of the ball on one main surface of the substrate was between 1,000 m and 1,500 m was defined as the friction coefficient. It should be noted that this measurement was performed in an environment of 25±2° C.

Example 1

The relationship between the lamellar length and the friction coefficient was evaluated by measuring the lamellar length and the friction coefficient for 27 samples of the lubricating oil compositions. FIG. 1 shows the relationship between the lamellar length and the friction coefficient.

From the results shown in FIG. 1, the correlation coefficient between the lamellar length and the friction coefficient was −0.93, and a correlation was observed between the lamellar length and the friction coefficient. In Example 1, it was found that by selecting a lubricating oil composition having a lamellar length within a specific range, a lubricating oil composition having a friction coefficient within a desired range could be selected.

For example, in FIG. 1, when the lamellar length of the lubricating oil composition exceeds A, a lubricating oil composition having a friction coefficient of less than B can be selected. Further, in FIG. 1, when the lamellar length of the lubricating oil composition is less than A, a lubricating oil composition having a friction coefficient exceeding B can be selected.

Example 2

Figure 2:
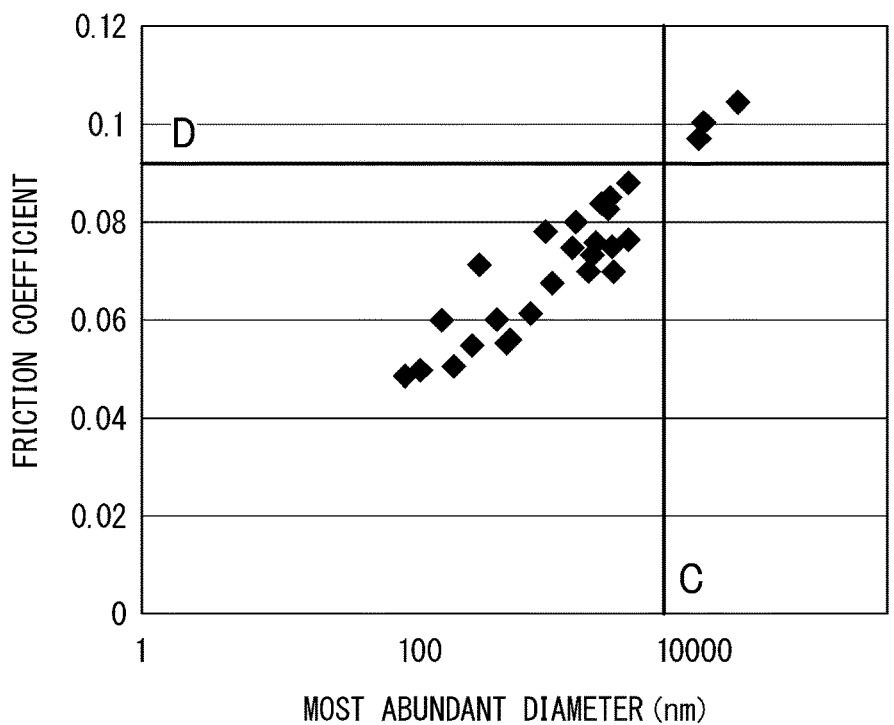
FIG. 2 is a view showing a relationship between a most abundant diameter of a lubricating oil composition and a friction coefficient in Example 2.

The relationship between the most abundant diameter and the friction coefficient was evaluated by measuring the most abundant diameter and the friction coefficient for 27 samples of the lubricating oil compositions. FIG. 2 shows the relationship between the most abundant diameter and the friction coefficient.

From the results shown in FIG. 2, the correlation coefficient between the most abundant diameter and the friction coefficient was 0.78, and a correlation was observed between the most abundant diameter and the friction coefficient. In Example 2, it was found that by selecting a lubricating oil composition having the most abundant diameter within a specific range, a lubricating oil composition having a friction coefficient within a desired range could be selected.

For example, in FIG. 2, when the most abundant diameter of the lubricating oil composition exceeds C, a lubricating oil composition having a friction coefficient exceeding D can be selected. Further, in FIG. 2, when the most abundant diameter of the lubricating oil composition is less than C, a lubricating oil composition having a friction coefficient of less than D can be selected.

Comparative Example 1

Figure 3:
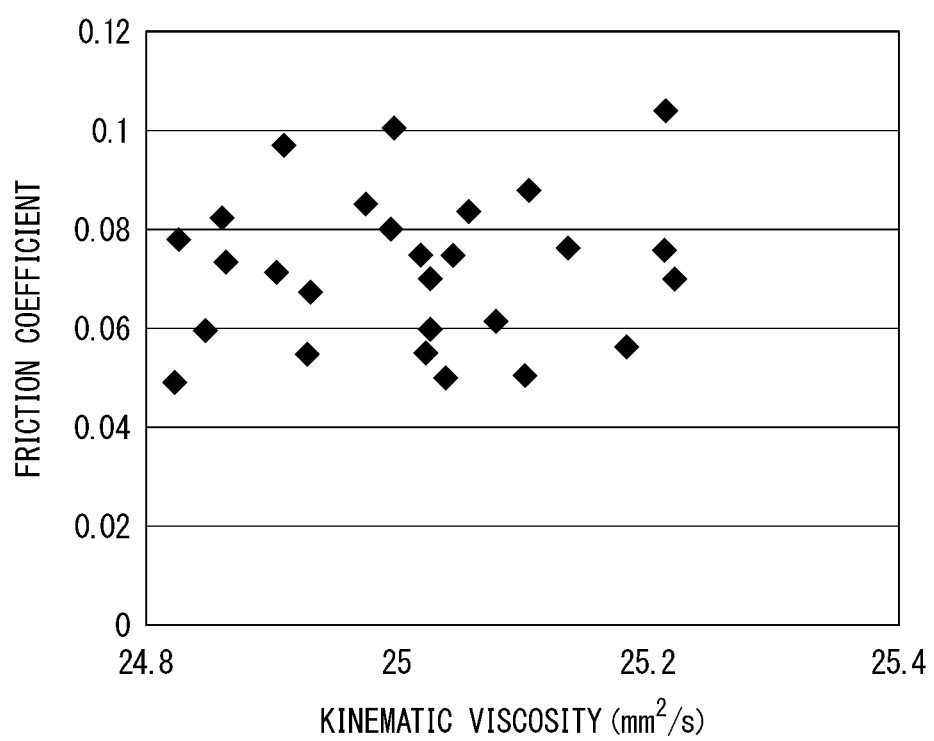
FIG. 3 is a view showing a relationship between a kinematic viscosity of a lubricating oil composition and a friction coefficient in Comparative Example 1.

The relationship between the kinematic viscosity and the friction coefficient was evaluated by measuring the kinematic viscosity and the friction coefficient for 27 samples of the lubricating oil compositions. FIG. 3 shows the relationship between the kinematic viscosity and the friction coefficient.

From the results shown in FIG. 3, the correlation coefficient between the kinematic viscosity and the friction coefficient was 0.11, and no correlation was observed between the kinematic viscosity and the friction coefficient. Therefore, it was found that the lubricating oil composition could not be selected by specifying the friction coefficient of the lubricating oil composition from the kinematic viscosity of the lubricating oil composition.

INDUSTRIAL APPLICABILITY

According to the present invention, in the process of producing a lubricating oil composition containing a base oil and a fullerene, by measuring at least one of the lamellar length of the lubricating oil composition and the most abundant diameter in the particle size distribution obtained by the dynamic light scattering method, and using the measured values, it is possible to suppress the deviation in frictional characteristics between the production batches. Therefore, the present invention is effective for suppressing a metal part from being damaged or worn in a sliding part of an automobile, a household electric appliance, an industrial machine, or the like.

The invention claimed is:

1. A method for inspecting a lubricant oil composition containing a base oil and a fullerene, the method comprising:
   measuring at least one of a lamellar length of said lubricating oil composition and a most abundant diameter in a particle size distribution obtained by a dynamic light scattering method; and
   selecting said lubricating oil composition whose measured value is within a set range.

2. The method for inspecting a lubricating oil composition according to claim 1,
   wherein said lamellar length and said most abundant diameter are measured, and
   said lubricating oil composition having both measured values within set ranges is selected.

3. A method for producing a lubricating oil composition comprising a step of selecting a lubricating oil composition obtained by mixing a base oil and a fullerene by the method for inspecting a lubricating oil composition according to claim 1.

4. A method for producing a lubricating oil composition comprising a step of selecting a lubricating oil composition obtained by mixing a base oil and a fullerene by the method for inspecting a lubricating oil composition according to claim 2.

5. The method for inspecting a lubricating oil composition according to claim 1, wherein at least said lamellar length is measured.

6. The method for inspecting a lubricating oil composition according to claim 1, wherein at least said most abundant diameter is measured.

7. A method for producing a lubricating oil composition comprising a step of selecting a lubricating oil composition obtained by mixing a base oil and a fullerene by the method for inspecting a lubricating oil composition according to claim 5.

8. A method for producing a lubricating oil composition comprising a step of selecting a lubricating oil composition obtained by mixing a base oil and a fullerene by the method for inspecting a lubricating oil composition according to claim 6.

* * * * *